United States Patent [19]

Moreno

[11] Patent Number: 5,354,537

[45] Date of Patent: Oct. 11, 1994

[54] PIERCING AND SAMPLING PROBE

[75] Inventor: Mario Moreno, Durham, N.C.

[73] Assignee: Akzo N.V., Arnhem, Netherlands

[21] Appl. No.: 874,371

[22] Filed: Apr. 27, 1992

[51] Int. Cl.$^5$ .................. B01L 3/02; A61M 5/158
[52] U.S. Cl. .................. 422/100; 73/864.01; 604/274; 604/239; 128/763
[58] Field of Search .............. 422/100, 103; 604/289, 604/272–274, 256, 247, 8–10, 53, 166; 128/214.6, 213.9, 213 R, 763, 764; 73/864.01, 864.11

[56] References Cited

U.S. PATENT DOCUMENTS

| | | | |
|---|---|---|---|
| 2,717,600 | 9/1955 | Huber | 604/274 |
| 3,119,391 | 1/1964 | Harrison | 604/274 |
| 3,386,438 | 6/1968 | Stevens | 604/272 |
| 3,630,198 | 12/1971 | Henkin | 128/215 |
| 3,633,580 | 1/1972 | Knox | 604/274 |
| 3,882,849 | 5/1975 | Jamshidi | 604/239 |
| 4,335,718 | 6/1982 | Calabrese | 604/272 |
| 4,431,426 | 2/1984 | Groshong et al. | 604/280 |
| 4,932,936 | 6/1990 | Dykstra et al. | 604/51 |
| 5,002,535 | 3/1991 | Gross | 604/272 |
| 5,024,659 | 6/1991 | Sjostrom | 604/272 |
| 5,169,602 | 12/1992 | Pang et al. | 422/103 |

FOREIGN PATENT DOCUMENTS 2005519 10/1971 Fed. Rep. of Germany.
740221 3/1954 United Kingdom.
2090164 12/1981 United Kingdom.

OTHER PUBLICATIONS

"A simple disposable TEFLON capped reaction vial", Wolen; Analytical Chemistry, vol. 44, No. 14, Dec. 1972, p. 2418.

*Primary Examiner*—Robert J. Warden
*Assistant Examiner*—Theresa A. Trembley
*Attorney, Agent, or Firm*—Spencer, Frank & Schneider

[57] ABSTRACT

A needle suitable for piercing a septum of a vacuum sealed container and through which a measured fluid sample from the container may be withdrawn. The needle is capable of withdrawing fluid from small sample volumes, such that the dead volume remaining in the sealed container is reduced. The needle has an elongated body having a longitudinal axis, an unobstructed bore therethrough along the longitudinal axis, a free end, and an end region adjacent said free end which has a slight conical taper toward said free end at a predetermined angle relative to the longitudinal axis. The free end includes an oblique cut through the conically tapered end region at an angle relative to the longitudinal axis being substantially larger than the predetermined angle of the taper so as to produce an elliptical opening at the free end. The elliptical opening lies along a plane diagonal to the longitudinal axis. This produces a toe or tip that is reduced in height allowing for a decrease in dead volume.

10 Claims, 2 Drawing Sheets

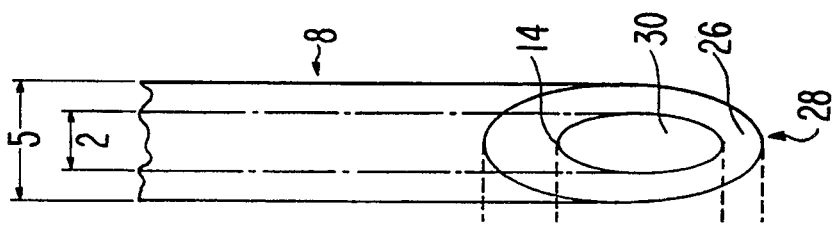
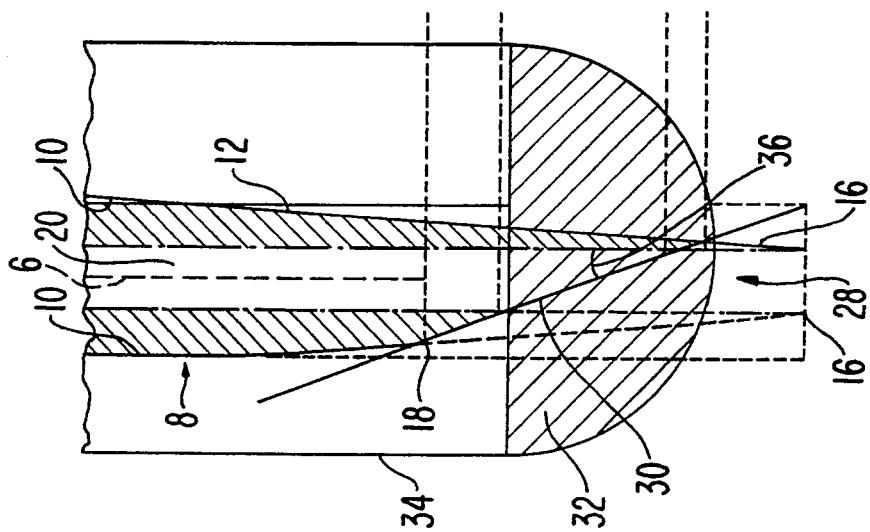
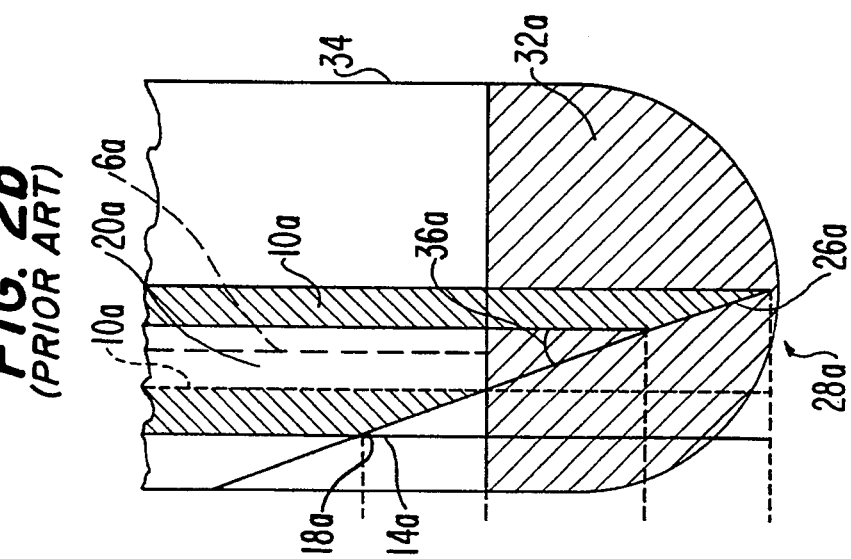
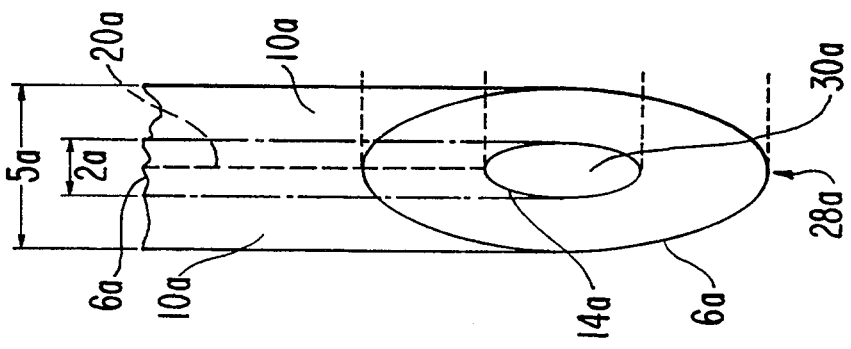

PIERCING AND SAMPLING PROBE

BACKGROUND OF THE INVENTION

1. Field of the Invention

The present invention relates to a method and apparatus for withdrawing a measured fluid sample from a container and, more particularly, for use in an automated blood/plasma sampling system, for example as disclosed in U.S. patent application Ser. No. 07/443,951, filed Dec. 1, 1989, by William C. Hulette, et al. assigned to the same assignee as the present application the subject matter of which is incorporated herein by reference.

2. Description of the Related Art

Fluid samples, such as blood or plasma, are stored in containers, such as test tubes, which are vacuum sealed by way of a rubber septum that must be pierced in order to withdraw a measured amount of the sample for testing purposes.

Known needles or piercing and sampling probes withdraw samples from these vacuum sealed containers, e.g. Vacutainers (TM), by means of a two part device. These sampling devices include an outer piercing sheath having a beveled edge for piercing the septum and, an inner, more narrow sampling probe which may be lowered through the outer sheath into the vacuum sealed container to withdraw a measured amount of fluid for testing. In this known mechanism, the tip of the inner, more narrow sampling probe comprises a flat edge, as it is not required to pierce the septum. This flat edge provides greater accuracy in the withdrawing and delivery of the fluid sample.

However, there are several disadvantages with this type of coaxial piercing and sampling probe arrangement. First, it involves a two step process, piercing the septum with the outer, larger diameter sheath and lowering the inner, more narrow sampling probe through the sheath into the vacuum sealed container to withdraw the test sample. This process is somewhat cumbersome as it requires two separate drive mechanisms, one for the outer sheath and another for the sampling probe itself. This complexity adds to the overall expense of the device.

Another known device involves a piercing and sampling probe having a single needle with a beveled edge which is used to pierce the septum of the vacuum sealed container and through which a measured fluid sample may be withdrawn. One problem with this device is that for small sample volumes, the angle of the bevel needed to pierce the septum is too steep so that a lot of dead volume remains in the sample container. That is, when the needle abuts the bottom of the sample container, the height of the elliptical opening at the needle tip causes the needle to begin drawing in air while a relatively large residual volume of sample still remains in the container.

SUMMARY OF THE INVENTION

It is an object of the present invention to reduce the complexity and cost of the known piercing and sampling probe mechanisms described above.

It is a further object of the invention to provide a means for extracting samples from a vacuum sealed container which significantly reduces the possibility of septum coring.

It is yet another object of the invention to minimize unused sample fluid due to the bevel of the needle of the sampling probe.

The above and other objects of the invention are accomplished by the provision of a needle suitable for piercing a septum of a vacuum sealed container and through which a measured fluid sample from the container may be withdrawn, comprising: an elongated body having a longitudinal axis, an unobstructed bore therethrough along the longitudinal axis, a free end, and an end region adjacent the free end which has a slight conical taper toward the free end at a predetermined angle relative to the longitudinal axis, the free end comprising an oblique cut through the conically tapered end region at an angle relative to the longitudinal axis, the angle being substantially larger than the predetermined angle of the taper so as to produce an elliptical opening at the free end on a plane diagonal to the longitudinal axis.

In a further aspect of the invention there is provided a piercing and sampling probe for piercing a septum of a vacuum sealed container and withdrawing a measured fluid sample from the container, comprising: an elongated body having a longitudinal axis, a bore therethrough along the longitudinal axis, a first longitudinal section having an inner diameter defining a volume for holding a measured fluid sample, and a second longitudinal section constituting a needle integrally connected to the first longitudinal section for piercing the septum of the vacuum sealed container, withdrawing the fluid sample and passing it into the first longitudinal section, the second longitudinal section having inner and outer diameters of more narrow dimensions than that of the first longitudinal section, the second longitudinal section having a free end, wherein an end region adjacent the free end is conically tapered at a predetermined angle relative to the longitudinal axis and an oblique cut through the conically tapered end region is made at an angle relative to the longitudinal axis substantially larger than the predetermined angle of the taper to produce an elliptical opening having a plane diagonal to the longitudinal axis.

Compared with a conventional sampling needle, the invention provides a number of advantages, including: 1) a reduced dead volume left in the sample container; 2) an increased pipetting accuracy; 3) enhanced washing and decontamination characteristics; 4) reduced sample-to-sample carry over; 5) a reduced amount of drop formation which affects sample volume accuracy; and, 6) a substantial elimination of septum coring.

The above and other advantages and feature of the invention allow the needle and probe to be used in many applications involving precise pipetting and measurement of fluids.

BRIEF DESCRIPTION OF THE DRAWINGS

A preferred embodiment of the invention will be described in conjunction with the accompanying drawings, wherein:

FIG. 2a is a front elevational view of a prior art device.

FIG. 2b is a side sectional view of a prior art device following aspiration of a liquid.

FIG. 3a is a front elevational view, similar to FIG. 2a, of the device in accordance with the invention.

FIG. 3b is a side sectional view, similar to FIG. 2b, of the device in accordance with the invention after aspiration of a liquid.

DETAILED DESCRIPTION OF THE INVENTION

Figure 1:
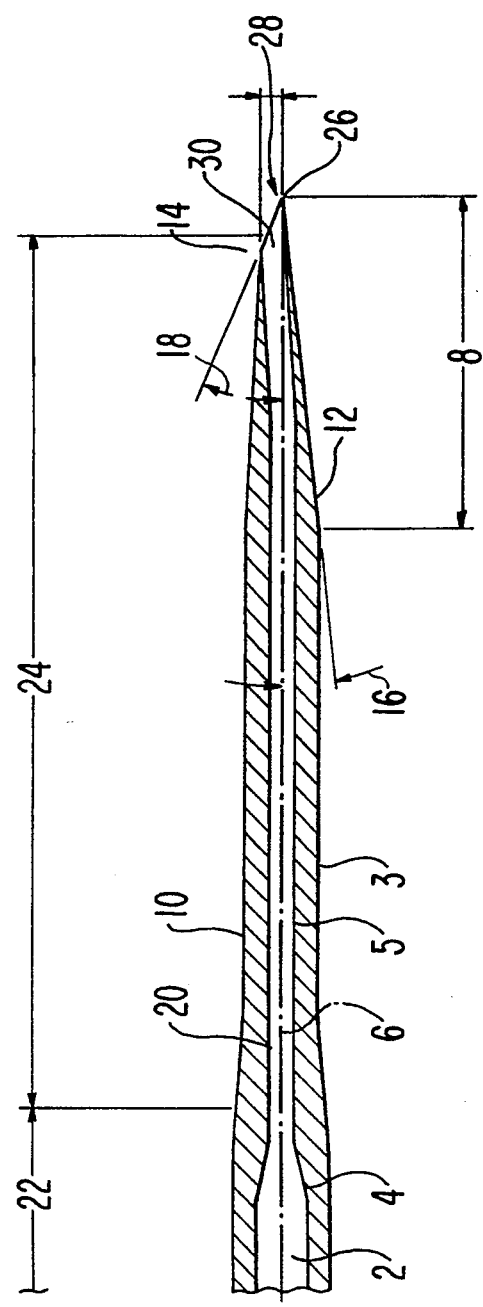
FIG. 1 is a side cross-sectional view of the invention.

Referring now to the drawings, FIG. 1 shows one embodiment of the present invention. An elongated body 10 is shown having a longitudinal axis 6. An unobstructed bore 20 is located within elongated body 10 and generally centered about its longitudinal axis 6. A first longitudinal section 22 has an inner diameter 2 defining a volume for holding a measured fluid sample and a transition region 4. A second longitudinal section constituting a needle 24 is integrally connected to the first longitudinal section 22 by way of transition region 4 for piercing the septum of a vacuum sealed container (e.g. a Vacutainer) not shown and withdrawing fluid.

The second longitudinal section (or needle) 24 has an inner and outer diameter of more narrow dimensions than that of the first longitudinal section. The second longitudinal section 24 has a free end 28 and an end region 8 adjacent to the free end. The end region 8 of second longitudinal section 24 has a slight conical taper toward free end 28 at a predetermined angle, for example 1°–3°, relative to longitudinal axis 6.

The free end 28 comprises an oblique cut 18 through the conically tapered end region at an angle 36 (see FIG. 3b) relative to longitudinal axis 6 which is substantially larger than the predetermined angle 16 of the conical taper. For example angle 36 may be on the order of about 20°. Oblique cut 18 produces an elliptical opening 30 at the free end 28 on a plane diagonal to longitudinal axis 6. Additionally, oblique cut 18 of free end 28 has a heel portion 14 and a toe portion 26.

Finally, end region 8 is deflected at a bend location 12 such that toe portion 26 of free end 28 aligns along longitudinal axis 6 of elongated body 10. In a preferred embodiment the length of end region 8 may be on the order of 0.25" and bend location 12 may be about 0.15" from free end 28.

FIG. 2a shows a front elevational view of a prior art type of piercing and sampling probe or needle. An elongated body 10a is shown having a longitudinal axis 6a. An unobstructed bore 20a is located within elongated body 10a and substantially centered about its longitudinal axis 6a. A constant inner diameter 2a and outer diameter 5a proceed the length of bore 20a. An oblique cut 18a at an angle 36a of 20° provides an elliptical opening 30a at free end 28a of elongated body 10a. Oblique cut 18a has a toe portion 26a and heel portion 14a.

FIG. 2b shows a side sectional view of the prior art piercing and sampling probe or needle of FIG. 2a with its end fully inserted into a test tube type container 34 containing a sample fluid which just reaches the bottom of heel portion 14a. As can be seen, a dead volume of sample fluid 32a can not be withdrawn from container 34 since an attempt to aspirate additional sample fluid would draw at most an air sample mixture not suitable for precise measurement and testing.

FIG. 3b shows a side sectional view of a piercing and sampling probe or needle in accordance with the present invention, after withdrawing a fluid sample. Elongated body 10 has been conically tapered from end region 8 toward free end 28 at a predetermined angle 16, in this example 2°, relative to a line parallel to longitudinal axis 6, and an oblique cut 18 at an angle of 20° has been made through conically tapered end region 8. The oblique cut 18 forms elliptical opening 30 through unobstructed bore 20. As can be seen, a dead volume of fluid 32 remains in container 34 following aspiration of the fluid sample to the bottom of heel portion 14. However, the level of the dead volume is lower by a significant amount relative to the dead volume level shown in FIG. 2b. This effect is brought about because of the slight conical taper in end region 8 which makes toe portion 26 significantly shorter in height than its prior art counterpart (26a of FIG. 2a), thus allowing more sample to be aspirated without withdrawing air.

According to a further aspect of the invention, heel portion 14 is passivated or rounded for example by glass powder blasting or suitable chemical treatment. Heel passivation aids in minimizing the possibility of coring a rubber septum in a piercing operation.

In operation, the piercing and sampling probe or needle of the invention is used to obtain accurate and precise sample volumes for measuring and testing in a manual or automated sampling system. The toe portion 26 of elongated body 10 initially pierces the rubber septum (not shown) of a vacuum sealed container 34, which contains a fluid sample, and slices a path therethrough. Heel portion 14 follows the path of toe portion 26 through the rubber septum. The heel portion has been passivated and rounded to prevent septum coring during entry which could plug up bore 20. The free end 28 of end region 8 is preferably deflected at bend location 12 such that toe portion 26 aligns along the longitudinal axis of elongated body 10. In a preferred embodiment, this alignment provides less stress about toe portion 26 during septum entry. In addition the 20° oblique cut 18 provides a sufficiently sharp point to facilitate penetration of the septum.

Entry of elongated body 10 into container 34 continues until toe portion 26 reaches the bottom of the container. A reverse vacuum pressure is applied through the unobstructed bore 20 of elongated body 10 to aspirate a measured volume of sample fluid into a graduated reservoir. In the case of a piercing and sampling probe, the elongated body 10 may be made of stainless steel and comprise a first longitudinal section 22 having an inner diameter 2 defining a volume for holding the measured fluid sample, and a second longitudinal section 24, having a smaller inner and outer diameter than first section 22 (constituting a needle) and integrally connected to the first longitudinal section 22 for piercing the septum of the vacuum sealed container. The reduction in diameter may be accomplished by swaging as will be understood by those skilled in the art.

In a further aspect of the invention a needle having the shape of second longitudinal section 24 may comprise a separate element which can be inserted into a graduated syringe or the like for withdrawing a measured fluid sample.

The narrower inner diameter 5 of bore 20 should be sufficiently small in respect to the viscosity of the sample fluid so that surface tension of the sample fluid at the free end will balance a vertical column of sample fluid in the elongated body without dripping. Proper sizing of the inner diameter will thus eliminate a potential source of inaccuracy in measurement. Additionally, the inner and outer surfaces of elongated body 10 may be coated with a non-stick coating, such as Teflon (Polytetraflorethylene). This coating serves to facilitate washing of the needle or probe so as to prevent cross-sample contamination. If a non-stick coating is applied to the inner surface of elongated body 10, narrowed inner diameter 5 must be sufficiently large so that the non-stick coating will not block bore 20. In the case of Teflon (Polytetrafluorethylene), the minimum diameter of bore 20 is about 0.012″ before blockage is likely to occur during application of the Teflon (Polytetrafluorethylene) coating.

The advantage of the instant probe can be significant when, for example, the sample is a pediatric blood serum sample. An infant provides very little blood sample from a needle stick in e.g. his or her heel, etc. Therefore, to avoid repeated painful needle sticks of the child, laboratory technicians are forced to work with a very small sample size. Hence, accurate sampling and testing of blood product must necessarily be done with the limited supply on the first try. It is therefore very important that the lab technician be able to use as much of the available sample as possible.

While there have been described what are presently believed to be the preferred embodiment of the invention, it will be apparent to one skilled in the art that numerous changes can be made in the structure, proportions and conditions set forth in the foregoing embodiments without departing from the invention as described herein and as defined in the appended claims.

What is claimed is:

1. A needle suitable for piercing a septum of a vacuum sealed container and through which a measured fluid sample from the container may be withdrawn, comprising:

an elongated body having a longitudinal axis, an unobstructed bore therethrough along the longitudinal axis, a free end, and an end region adjacent said free end which has a conical taper toward said free end at a predetermined angle relative to the longitudinal axis, said free end comprising an oblique cut through the conically tapered end region at an angle relative to the longitudinal axis, said free end further comprising a toe portion which initially encounters a septum and slices a path therethrough and a heel portion which follows the path of the toe portion, said toe portion and said heel portion each having a respective height measured along the longitudinal axis, said heel portion being passivated so as to prevent septum coring, and said angle being substantially larger than the predetermined angle of the conical taper so as to produce an elliptical opening at the free end on a plane diagonal to the longitudinal axis whereby said toe portion is reduced in height relative to said heel portion height.

2. A needle as recited in claim 1, wherein said free end is deflected such that the toe portion aligns along the longitudinal axis of said elongated body.

3. A needle as recited in claim 1, further comprising a non-stick coating on inner and outer surfaces of said elongated body.

4. A needle as recited in claim 1, wherein said elognated body has an inner diameter which is sufficiently small so that surface tension of the sample fluid at the free end will balance a vertical column of sample fluid in said needle.

5. A needle as recited in claim 4, wherein the inner diameter of said needle is made sufficiently large to be capable of receiving a non-stick coating without blocking the unobstructed bore.

6. A piercing and sampling probe for piercing a septum of a vacuum sealed container and withdrawing a measured fluid sample from the container, comprising:

an elongated body having a longitudinal axis, a bore therethrough along the longitudinal axis, a first longitudinal section having an inner diameter defining a volume for holding a measured fluid sample, and a second longitudinal section constituting a needle integrally connected to said first longitudinal section for piercing a septum of a vacuum sealed container, withdrawing the fluid sample and passing it into said first longitudinal section, said second longitudinal section having inner and outer diameters of more narrow dimensions than that of said first longitudinal section, said second longitudinal section having a free end and an end region adjacent said free end which has a conical taper toward said free end at a predetermined angle relative to the longitudinal axis, said free end comprising an oblique cut through said conically tapered end region at an angle relative to the longitudinal axis, said conically tapered end region further comprising a toe portion which initially encounters the septum and slices a path therethrough and a heel portion which follows the path of the toe portion, said toe portion and said heel portion each having a respective height measured along the longitudinal axis, said heel portion being passivated so as to prevent septum coring, and said angle being substantially larger than the predetermined angle of the conical taper so as to produce an elliptical opening at the free end on a plane diagonal to the longitudinal axis whereby said toe portion is reduced in height relative to said heel portion height.

7. A piercing and sampling probe as recited in claim 6, wherein said free end is deflected such that the toe portion aligns along the longitudinal axis of said elongated body.

8. A piercing and sampling probe as recited in claim 6, further comprising a non-stick coating on inner and outer surfaces of said elongated body.

9. A piercing and sampling probe as recited in claim 6, wherein the inner diameter of said second longitudinal section is sufficiently small so that surface tension of the sample fluid at the free end will balance a vertical column of sample fluid in said piercing and sampling probe.

10. A piercing and sampling probe as recited in claim 9, wherein the inner diameter of said needle is sufficiently large to be capable of receiving a non-stick coating without blocking the bore.

* * * * *